(12) United States Patent
Qian et al.

(10) Patent No.: US 12,082,584 B2
(45) Date of Patent: Sep. 10, 2024

(54) BOC-BUTENOLIDE, AN ANTIFOULING COMPOUND THAT HAS POTENT ABILITY TO INHIBIT THE SETTLEMENT OF MARINE INVERTEBRATE LARVAE

(71) Applicants: The Hong Kong University of Science and Technology, Hong Kong (CN); Southern Marine Science and Engineering Guangdong Laboratory (Guangzhou), Guangzhou (CN)

(72) Inventors: Peiyuan Qian, Hong Kong (CN); Ho Yin Chiang, Hong Kong (CN); Jinping Cheng, Hong Kong (CN)

(73) Assignees: The Hong Kong University of Science and Technology, Hong Kong (CN); Southern Marine Science and Engineering Guangdong Laboratory (Guangzhou), Guangzhou (CN)

(*) Notice: Subject to any disclaimer, the term of this patent is extended or adjusted under 35 U.S.C. 154(b) by 258 days.

(21) Appl. No.: 17/655,536

(22) Filed: Mar. 18, 2022

(65) Prior Publication Data
US 2022/0295795 A1    Sep. 22, 2022

Related U.S. Application Data

(60) Provisional application No. 63/163,001, filed on Mar. 18, 2021.

(51) Int. Cl.
| | |
|---|---|
| *A01N 47/12* | (2006.01) |
| *A01N 25/10* | (2006.01) |
| *A01P 15/00* | (2006.01) |
| *A61L 31/16* | (2006.01) |

(52) U.S. Cl.
CPC ............. *A01N 47/12* (2013.01); *A01N 25/10* (2013.01); *A01P 15/00* (2021.08); *A61L 31/16* (2013.01); *A61L 2300/216* (2013.01); *A61L 2300/404* (2013.01)

(58) Field of Classification Search
None
See application file for complete search history.

(56) References Cited

U.S. PATENT DOCUMENTS

| | | |
|---|---|---|
| 8,177,896 B2 | 5/2012 | Qian et al. |
| 8,557,331 B2 | 10/2013 | Qian et al. |
| 8,657,943 B2 | 2/2014 | Batista et al. |

OTHER PUBLICATIONS

Li. Biofouling, 2012, 28(8), 857-864 (Year: 2012).*
Wang, K.-L., et al., "Low-Toxicity Diindol-3-ylmethanes as Potent Antifouling Compounds," Mar Biotechnol, 2015, 17:624-632, supplemental p. 1.
Chiang, H.-Y., et al., "Synthetic Analogue of Butenolide as an Antifouling Agent," Marine Drugs, 2021, 19(481):1-12.

* cited by examiner

*Primary Examiner* — Noble E Jarrell
(74) *Attorney, Agent, or Firm* — Saliwanchik, Lloyd & Eisenschenk

(57) ABSTRACT

The subject invention pertains to compositions and methods of coating objects using BOC-butenolide. The invention also relates to compositions and methods for enhancing the performance and longevity of the coated objects with BOC-butenolide, including inhibiting fouling often caused by marine organisms.

11 Claims, 6 Drawing Sheets

BOC-BUTENOLIDE, AN ANTIFOULING COMPOUND THAT HAS POTENT ABILITY TO INHIBIT THE SETTLEMENT OF MARINE INVERTEBRATE LARVAE

CROSS-REFERENCE TO RELATED APPLICATION

This application claims the benefit of U.S. Provisional Application Ser. No. 63/163,001, filed Mar. 18, 2021, which is hereby incorporated by reference in its entirety including any tables, figures, or drawings.

BACKGROUND OF THE INVENTION

Biofouling has been a serious problem in maritime industry, and fouling on ship hulls or surfaces of the infrastructure causes tremendous amount of maintenance costs (Yebra et al. 2004). Previous, tributyltin-based coating or copper biocides were used for antifouling (AF) purpose. However, they are toxic to a wide range of non-target organisms (Alzieu 2000; Konstantinou and Albanis 2004).

Many bioactive marine natural products have been discovered. There are already 214 marine natural products and 23 synthetic analogs with high bioactivities isolated and tested in 2015 (Qian et al. 2015). Although many potent AF compounds have been discovered, rarely can those compounds be commercialized. Supplying the antifouling compounds hinders the development of AF paints based on the marine natural products (Dobretsov et al., 2006; Fusetani, 2011; Qian et al., 2010; Xu et al., 2010). Extracting marine natural products from microorganisms is one way to source the AF compounds, as microorganisms are able to produce a wide range of bioactive secondary metabolites (Dahms et al., 2006; Qian et al., 2007; Almeida and Vasconcelos, 2015). The convenience of bacterial cultivation and mass production of metabolites in a short period of time are advantageous over extracting compounds from macroorganisms (Dobrestov et al., 2006; Xu et al., 2010; Almeida and Vasconcelos, 2015).

Another way to solve the problem is by structural optimization using organic synthesis (Dobrestov et al., 2006). Secondary metabolites that usually have a complex structure may be difficult to synthesize in large quantities for commercial scale (Dobrestov et al., 2006). Pharmacophores, which are responsible for antifouling abilities, can be identified by studying the structure-activity relationship of bioactive compounds isolated from organisms (Li et al., 2012). Structure-activity relationship is the relationship between the chemical structure of a molecule and its biological activity (Greene, 2007). Primary screening is an important step that leads to optimization in the drug discovery processes (Guha, 2013) and for antifouling compound discovery. There are many benefits from structural optimization of the compound, for instance, the increase of potency, reduced toxicity of the original compound (Guha, 2013), improvement of physical or chemical properties of the compound, and simplified chemical structure for chemical synthesis.

A compound 5-octylfuran-2(5H)-one (butenolide) has been discovered to be promising AF compound. However, the melting point of butenolide is 23° C. and has a stinky smell, which makes it difficult to control the proportion of AF compound in the coatings precisely, as it will easily melt at room temperature (solid-liquid mixture in room temperature). Butenolide has a half-life of 30.5 days at 25° C.; a longer duration of efficacy will be appreciated in the practical usage (Chen et al., 2015).

Therefore, there remains a need to develop environmentally friendly AF coatings with reduced toxicity.

BRIEF SUMMARY OF THE INVENTION

This subject invention provides antifouling compositions and methods for inhibiting fouling, including, for example, the settlement of marine invertebrate larvae. Specifically, this invention pertains to antifouling compositions comprising a butenolide with a protecting group, such as, for example, Tert-butyl (5-(5-oxo-2,5-dihydrofuran-2yl)pentyl) carbamate (BOC-butenolide). In certain embodiments, BOC-butenolide is synthesized based on chemical structural modification strategy, which can be synthesized in large scale on request.

In certain embodiments, antifouling compositions are provided, comprising BOC-butenolide, and one or more surface coating ingredients. In certain embodiments, the surface coating ingredients include, for example, buffering agents, binders, solvents, pigments, or any other ingredient that composes, for example, paints, primers, lacquers or sealants.

In preferred embodiments, methods for inhibiting larval settlement, the methods comprising the application of BOC-butenolide onto a surface are provided. In certain embodiments, the addition of BOC-butenolide-based composition to the surface enhances the performance and/or longevity of the surface.

Advantageously, the subject invention provides eco-friendly AF methods for use. BOC-butenolide has a higher melting point (132° C.) when compared to butenolide (23° C.), which improves the control of the proportion of AF compound in the coatings. Also, BOC-butenolide is odorless and its stability is increased so that the AF coatings can have a better AF performance.

DETAILED DISCLOSURE OF THE INVENTION

Figure 1:
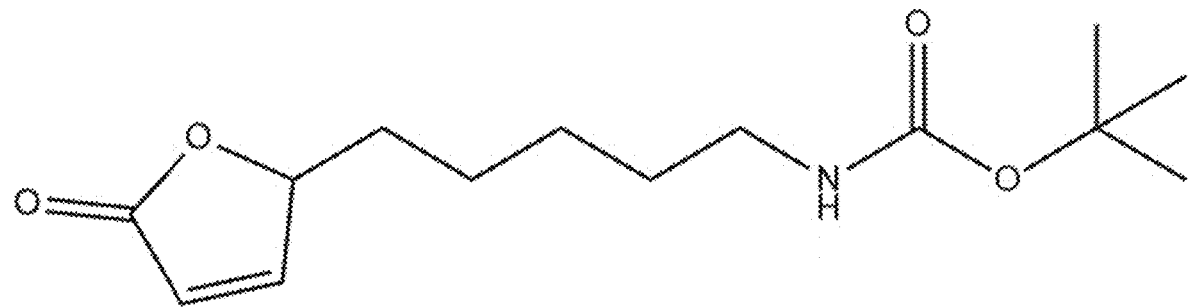
FIG. 1. Chemical structure of Tert-butyl (5-(5-oxo-2,5-dihydrofuran-2yl)pentyl)carbamate (BOC-butenolide).
Figure 2A:
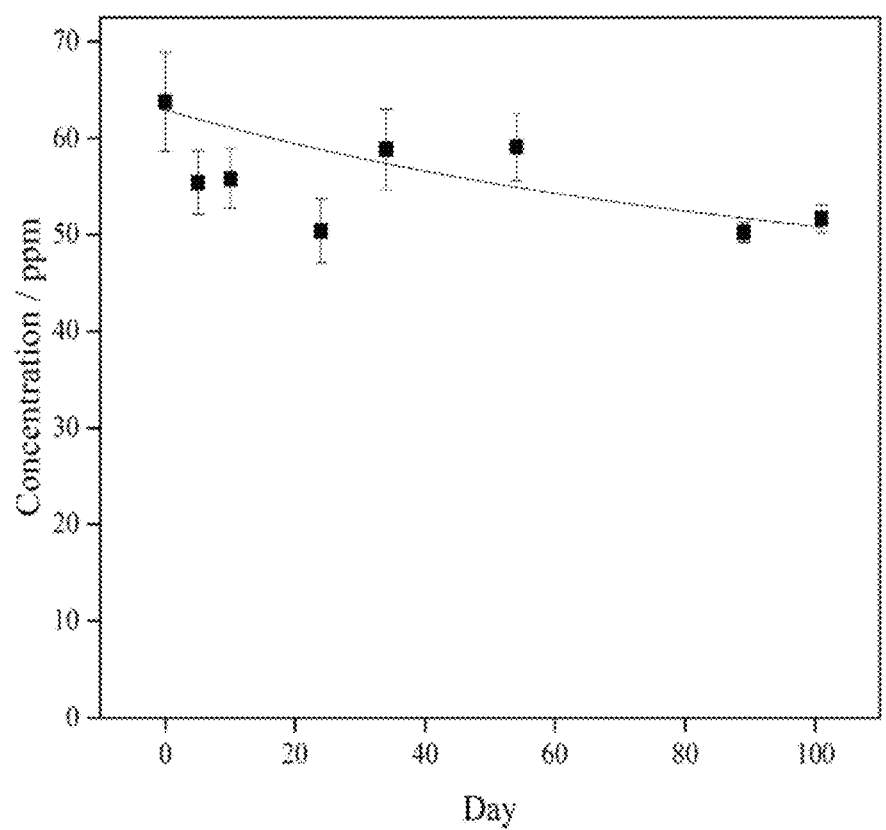
FIGS. 2A-2B. Measured concentrations of BOC-butenolide in ASW for 3 months (FIG. 2A) and working concentrations of BOC-butenolide (FIG. 2B) used in FIGS. 3-6 and FIGS. 8-9.
Figure 2B:
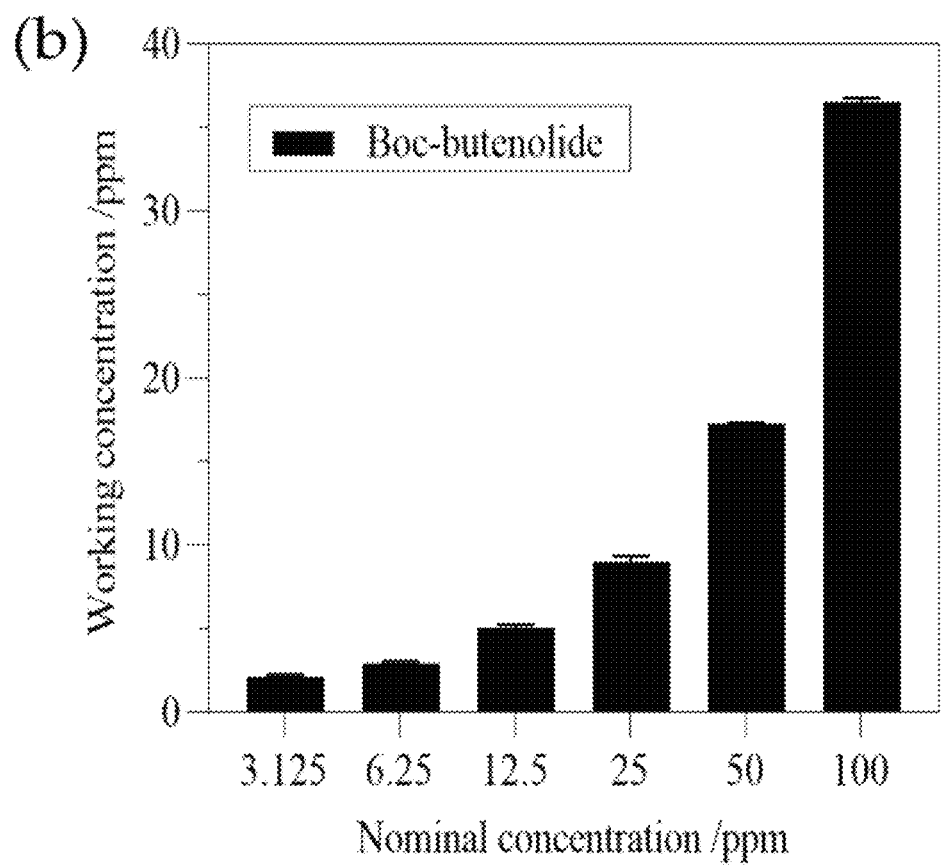

The subject invention provides compositions and method for inhibiting fouling, particularly of larval settlement. Specifically, the subject invention provides compositions and methods for the use of BOC-butenolide to inhibit fouling, including, for example, larval settlement. In certain embodiments, the anti-fouling composition can comprise antifouling compounds and/or coating ingredients.

Selected Definitions

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which depends in part on how the value is measured, i.e., the limitations of the measurement system. In the context of compositions containing amounts of ingredients where the terms "about" is used, these compositions contain the stated amount of the ingredient with a variation (error range) of 0-10% around the value (X±10%). In other contexts the term "about" is provides a variation (error range) of 0-10% around a given value (X±10%). As is apparent, this variation represents a range that is up to 10% above or below a given value, for example, X±1%, X±2%, X±3%, X±4%, X±5%, X±6%, X±7%, X±8%, X±9%, or X±10%.

In the present disclosure, ranges are stated in shorthand to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are explicitly included.

As used herein, an "isolated" or "purified" compound is substantially free of other compounds. In certain embodiments, purified compounds are at least 60% by weight (dry weight) of the compound of interest. Preferably, the preparation is at least 75%, more preferably at least 90%, and most preferably at least 99%, by weight of the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

By "reduces" is meant a negative alteration of at least 1%, 5%, 10%, 25%, 50%, 75%, or 100%.

By "increases" is meant as a positive alteration of at least 1%, 5%, 10%, 25%, 50%, 75%, or 100%.

As used herein, "cleaning" as used in the context of contaminants or fouling means removal or reduction of contaminants from a surface or an object. Cleaning can include treating, purifying, defouling, decontaminating, clearing or unclogging, and can be achieved by any means, including but not limited to, melting, dispersing, emulsifying, dissolving, scraping, degrading, blasting, soaking, or cleaving the contaminant. Cleaning can further include controlling, inhibiting or preventing further fouling or contamination from occurring.

As used herein, "contaminant" refers to any substance that causes another substance or object to become fouled or impure. Contaminants can be living or non-living and can be inorganic or organic substances or deposits. Living organisms can include bacteria, such as cyanobacteria, *Pseudomonas* spp., *Bacillus* spp., *Listeria* spp., *Staphylococcus* spp. *Lactobacillus* spp., and *Lactococcus* spp.; and eukaryotic organisms, such as algae, yeast, fungi, barnacles (e.g., *Balanus amphitrite*), tubeworms (*Hydroides elegans*), and mussels. Furthermore, contaminants can include, but are not limited to, scales, hydrocarbons, and dissolved organic matters, such as, for example, amino acids and proteins derived from biomass. Reference to "scale" means any type of scale that results from the precipitation of, for example, barium sulfate, calcium carbonate, calcium sulfate, calcium oxalate, magnesium hydroxide, magnesium oxide, silicates, strontium sulfate, aluminum oxide hydroxides, aluminosilicates, magnetite or nickel ferrite, sodium chloride, silicon dioxide, iron sulfide, iron oxides, iron carbonate, copper, phosphates, oxides, and any other mineral compound that can precipitate and form deposits.

As used herein, a "solvent" is any substance, gas, liquid, or solid, that dissolves a solute. Water is a common solvent in the present composition and methods.

As used herein, a "binder" is a substance that adheres the composition to the surface to which it is applied. In paints, a binder can hold together a pigment to a surface after the solvent has evaporated. Additionally, a "binder" can refer to a substance that can hold the components of a composition together. For example, in paint a binder can also hold the pigments in the paint together.

As used herein, "stability" generally refers to the reactivity of the composition. The composition is considered "stable" if it does not react in the environment in which it resides. The environment can be the surface and/or object to which the coating is applied. The environment can also be where the stored composition resides before application to the object or surface—also referred to as its "shelf life." A lack of reactivity is demonstrated based on the ability for the composition to retain its properties for a desired amount of time. A reaction may comprise corrosion, decomposition, polymerization, or ignition of the composition. Upon a reaction, the composition is either unstable or has outlasted its useful timeline.

According to the subject invention, a harmful accumulation of material, including living organisms or non-living substances results in the process of "fouling." "Fouling" can result in clogging, scaling, or other undesired buildup. "Fouling" can affect the efficiency, reliability, or functionality of the object.

As used herein, the term "effective amount" is used to refer to an amount of a compound or composition that, when applied or contacted to a surface or organism, is capable of inhibiting, preventing, or improving fouling. In other words, when applied or contacted to a surface or organism, the amount is "effective." The actual amount will vary depending on a number of factors including, but not limited to, the one or more substances that are causing the fouling being inhibited, prevented, or improved; the severity of the fouling; and the route of application.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BOC-Butenolide Compositions

The disclosure provides approaches for inhibiting fouling, particular by marine invertebrate larvae settlement, using compositions comprising a butenolide in which a protecting group is added to butenolide, according to formula (I) (Tert-butyl (5-(5-oxo-2,5-dihydrofuran-2yl)pentyl)carbamate). In preferred embodiments, the protecting group is tert-Butyl carbamate (BOC).

Formula (I)

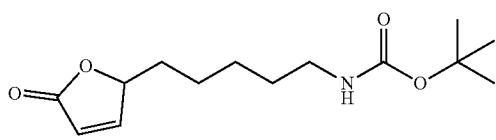

In the preferred embodiments, the compositions and methods according to the subject invention utilize BOC-butenolide, such as, for example, according to formula (I). BOC-butenolide may be added at a concentration of about 1 μg/mL to about 100 μg/mL, about 3.125 μg/mL to about 100 μg/mL, or about 25 μg/mL.

Preparation of Anti-Fouling Products

The BOC-butenolide of the subject invention can be obtained from organic synthesis by reacting butanolide with di-tert-butyl decarbonate at about 40° C. In preferred embodiments, BOC-butenolide can be further processed to form a coating. The coating can be prepared by mixing BOC-butenolide and polymer. In specific embodiments, BOC-butenolide can be added at a wt % of about 1% to about 20%, and the polymer, such as, for example, Poly(ε-caprolactone) or poly lactic acid, at a wt % of about 80% to about 99%. The mixtures can be dissolved in a solvent, such as, for example, xylene and tetrahydrofuran (THF) (with xylene to THF ratio v:v=1:3) at about 18° C. to about 25° C. After mixing into a homogenous solution, the solution can be applied onto a surface, the surface can be dried at about 18° C. to about 25° C. for at least about one week or enough time to remove the solvent, and the continuous coating can be formed. Coatings with different concentration of BOC-butenolide can be prepared with the above procedure.

In certain embodiment, the antifouling composition comprises a binder, for the adhesion purpose of the antifouling composition to a surface of objects. The binder can be selected from common polymers, acrylic, alkyds, acrylic acid, acrylamide, phenolic, phenolic-alkyd, polyacrylamide, polyurethanes, silicone-alkyd, polyesters, epoxies, vinyl, vinyl acetate-ethylene, vinyl-alkyd, inorganic binders (sodium, potassium ethyl silicate, lithium, etc.), organic binders (carbon-based), Tectyl® (Daubert Chemical Company, Inc., Chicago, IL), aliphatic-urethanes, and oil-modified urethanes, or other commercialized binder that have strong adhesion ability. In preferred embodiments, the polymer is poly(ε-caprolactone) based polyurethane (PCL-PU), according to formula (II).

Formula (II)

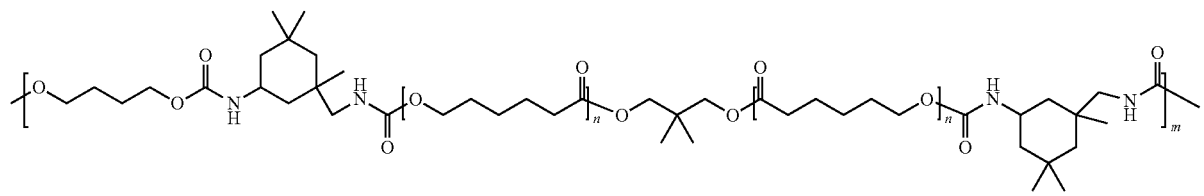

Wherein n can be about 1 to about 10 and m about 1 to about 10.

Further components can be added to enhance performance of the coatings. These additives can be biocides, pigments, buffers, solvent, adhesion-promoting compounds, or other ingredients for specific use.

In certain embodiments, the coating composition of the subject invention comprises a pigment or dye, which can provide the color of paints or other coatings but can additionally protect the surface or object from, for example, UV light. Pigments or dyes can be natural, synthetic, inorganic, or organic. The pigments or dyes can be selected from, for example, titanium dioxide, zin oxide, zinc yellow, yellow dyes, benzidine yellows, chrome oxide green, phthalocyanine green, phthalocyanine blues, ultramarine blue, vermillion, pigment brown 6, red 170, dioxazine violet, carbon black, iron (II) oxide, quartz sand ($SiO_2$), talc, barite ($BaSO_4$), kaoline clay, and limestone ($CaCO_3$).

In certain embodiments, one of the solvents used in the composition is selected from mineral or organic solvents, including, for example, ethanol, butanol, propanol, aliphatic hydrocarbons, alicyclic hydrocarbons, tetrahydrofuran (THF), xylene, toluene, ketones, and/or isopropyl alcohol. In a preferred embodiment, a combination of xylene and THF can be in an amount of 3 ml for every one gram of coating material is added as to the composition.

In one embodiment, the composition may further comprise buffering agents including organic and amino acids or their salts. Suitable buffers include, for example, citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used, but it is preferable to use natural buffers such as organic and amino acids or their salts listed above.

In a further embodiment, pH adjusting agents include potassium hydroxide, ammonium hydroxide, Potassium carbonate or bicarbonate, hydrochloric acid, nitric acid, sulfuric acid or a mixture.

The BOC-butenolide-based product may be applied with a composition that promotes adherence of the BOC-butenolide-based product to a surface to be treated. The adhesion-promoting substance may be a component of the BOC-butenolide-based product or it may be applied simultaneously or sequentially with the BOC-butenolide-based product.

Other additives typically used in coating compositions may be used, including water softening agents, sequestrants, corrosion inhibitors, and antioxidants, which are added in amounts effective to perform their intended function. Identification and use of these additives, and amounts thereof, is well within the skill of the art. Suitable water softening agents include linear phosphates, styrene-maleic acid copolymers, and polyacrylates. Suitable sequesterants include 1,3-dimethyl-2-immidazolidinone; 1-phenyl-3-isoheptyl-1, 3-propanedione; and 2 hydroxy-5-nonylacetophenoneoxime. Examples of corrosion inhibitors include 2-aminomethyl propanol, diethylethanolamine benzotraizole, and methyl benzotriazole. Antioxidants suitable for the present invention include (BHT) 2,6-di-tert-butyl-para-cresol, (BHA) 2,6-di-tert-butyl-para-anisole, Eastman inhibitor O A B M-oxalyl bis (benzylidenehydrazide), and Eastman DTBMA 2,5-di-tert-butylhydroquinone.

In certain embodiments, the composition further comprises salts and/or mineral salts selected from phosphorous, magnesium, potassium, glucose and ammonium. Preferably, from 1 to 20 g/L, and more preferably from 2 to 10 g/L of ammonium salt is added, for example, ammonium phosphate, diammonium phosphate, ammonium chloride, or another dibasic or monobasic salt.

Other suitable additives, which may be contained in the formulations according to the invention, include substances that are customarily used for such preparations. The additives can be, for example, carriers, viscosity modifiers, preservatives, tracking agents, biocides, driers, plasticizers, flow control agents, defoamers, emulsifiers, UV stabilizers, anti-skinning agents, texturizers, emulsifying agents, lubricants, solubility controlling agents, preservatives, and/or stabilizers.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. The storage time can be 1 year for maximum, and the preferred temperature for storing can be at about room temperature.

The compositions according to the subject invention can comprise ingredients in amounts effective to clean the surfaces, formations, and equipment, and/or to provide an effective coating to prevent future buildup of contaminants, scale and corrosion.

Use of BOC-Butenolide in Antifouling Compositions

In preferred embodiments, methods are provided for applying an antifouling composition onto a submerged surface that can be fouled with marine invertebrates, wherein BOC-butenolide is applied onto a surface or directly to marine invertebrates' larvae. The use of antifouling composition with the subject invention can provide improvements for antifouling uses. The subject invention is not an exhaustive examination of all applications.

The anti-fouling compositions of the subject invention can be applied to a variety of inorganic or organic object surfaces such as, for example, metals including stainless steel, aluminum, titanium; organic matter including wood, rubber; plastics; minerals; glass; and concrete. The surfaces can be used in a variety of industries including medical device, petroleum, aquaculture, and fishing. The surfaces can be ships, hulls, tubing, pipes, needles, pumps, propellers, buoys, and ropes. The compositions can be applied to objects in a range of temperatures or aquatic environments. The antifouling compositions can be added to a traditional coating product such as a paint, stain, adhesive, primer, sealant, finish, varnish, polish, lacquer, an anti-fouling substance, and/or an anti-abrasive substance.

In certain embodiments, BOC-butenolide can inhibit the settlement or formation of marine organisms. These organisms can include microscopic or macroscopic organisms, including bacteria, algae, and marine invertebrate larvae.

In certain embodiments, the subject compositions can increase the longevity of the object by preventing fouling by living organisms or non-living substances. The subject invention can be used for preventing deposition from occurring. Dispersal, or dissolution, of organisms or precipitates decreases the concentration of contaminants available on the surface or object. Thus, the present invention allows for delaying or completely removing the necessity for preventative maintenance related to removing precipitates and deposits, as well as the need for replacing or repairing equipment parts. The subject coating composition can further be applied for the dispersal of scale buildup in, for example, storage and transportation tanks, tankers, ships, pipelines and flowlines, concrete, asphalt, and metals without need for mechanical cleaning solutions or toxic solvents.

In certain embodiments, the methods are used to clean a surface, wherein the surface is equipment or devices in need of decontamination, defouling, and/or unclogging. Advantageously, the methods of the subject invention can be used to improve overall productivity of an industrial operation or a piece of equipment by improving the maintenance and proper functioning of equipment.

The composition can be applied to the surface by spraying using, for example, a spray bottle or a pressurized spraying device. The composition can also be applied using a cloth or a brush, wherein the composition is rubbed, spread or brushed onto the surface. Furthermore, the composition can be applied to the surface by dipping, dunking or submerging the surface into a container having the composition therein.

In one embodiment, the material and/or surface can be allowed to soak with the composition thereon for a sufficient time to apply the coating or lift and/or remove the contaminant from the object and/or surface. For example, soaking can occur for at least 5 seconds, 30 seconds, 1 minute, 30 minutes, 60 minutes, 12 hours, 24 hours, 36 hours, 48 hours, or 72 hours or more, as needed.

In one embodiment, the method further comprises the step of removing the composition and contaminant from the surface. This can be achieved by, for example, rinsing or spraying water onto the surface, and/or rubbing or wiping the surface with a cloth until the composition and contaminant have been freed from the surface. Rinsing or spraying with water can be performed before and/or after rubbing or wiping the surface with a cloth.

In another embodiment, mechanical methods can be used to remove the contaminant and/or composition from the surface. For example, an agitator, drill, hammer, or scraper can be used for freeing contaminants from surfaces that are particularly difficult to remove due to, for example, the amount of contaminant or the type of contaminant.

In certain embodiments, BOC-butenolide can be released from the subject compositions after application to an object and/or surface at a rate of about 140 μg $cm^{-2}$ $day^{-1}$ to about 150 $cm^{-2}$ $day^{-1}$.

Materials and Methods

Determination of Working Concentration and Stability Using High-Performance Liquid Chromatography (HPLC)

The stock concentrations of BOC-butenolide were made by dissolving 100 mg of BOC-butenolide in 1 mL of DMSO to make a stock of 100 mg/mL, stored at −20° C. The BOC-butenolide samples used in the larval settlement and mortality experiments were prepared by serial dilution of stock concentrations of BOC-butenolide using ASW as the diluent, and the DMSO content in final samples were lower than 0.5‰ v/v.

The measurement and analysis of BOC-butenolide were performed according to previous reports [Chen et al., 2015; Ma et al., 2017]. The preparation of nominal concentrations for BOC-butenolide was described in the section of "Chemicals and seawater". The calibration standards were prepared by serial dilutions of stock concentrations of BOC-butenolide using methanol as the diluent, and the DMSO content in all calibration standard samples was lower than 0.5‰ v/v. The stock concentrations of BOC-butenolide were made by dissolving 500 mg of BOC-butenolide in 1 mL of DMSO to make a stock of 500 mg/mL and stored at about −20° C. The working concentrations of BOC-butenolide samples used in settlement bioassay were measured by reverse-phase HPLC using a Waters 2695 separation module coupled to a Waters 2669 photo-diode array (PDA) detector according to the peak area at 210 nm (Waters Corporation, Taunton, MA, USA). Identification of BOC-butenolide was determined based on its retention times (BOC-butenolide, 6.8±0.1 min). The samples were tested with a 20 min gradient of 50-99% aqueous acetonitrile (ACN) containing 0.05% v/v trifluoroacetic acid (TFA) at a flow of 1 mL/min. The working concentrations of BOC-butenolide were calculated according to their standard curves using peak areas plotted against known quantities of standards. The recoveries for BOC-butenolide was 99.5%.

The stability of BOC-butenolide was measured by the concentration changes of BOC-butenolide in ASW throughout 3 months. The starting nominal concentration of BOC-butenolide was 200 ppm. At every time point, 5 mL of the solution was drawn and mixed with 10 mL dichloromethane (DCM). The DCM fraction with the analyte was dried under nitrogen gas, redissolved reconcentrated in 1 mL of methanol and subjected to above HPLC analysis.

Collection of *Amphibalanus amphitrite* Larvae Sample

Adult *A. amphitrite* colonies were collected from Tso Wo Hang Pier (22°23'32.1"N 114°17'18.7"E), Hong Kong, from April to June 2018. The adults were kept in a water tank with running seawater at the Coastal Marine Laboratory (the Hong Kong University of Science and Technology) for no more than a week before experimental use. Adults were induced under light sources for 1 h to hatch and the larvae were obtained using the method described previously by Harder et al. (2001), which is hereby incorporated by reference in its entirety. The nauplii larvae newly released from the adults were reared on diatom *Chaetoceros gracilis* Schütt. The seawater culture medium was replaced with fresh FSW and algae every day, and the nauplii reached the competent stage, known as cyprid, after 4 d of incubation at around 28° C.

Collection of *Hydroides elegans* Larvae Sample

Adult *H. elegans* colonies were collected from a fish farm at Yung Shue O, Hong Kong (22°24'N, 114°21'E) from March to April 2019. The adults were kept in a water tank with running seawater at the Coastal Marine Laboratory (the Hong Kong University of Science and Technology) for no more than 3 days before experimental use. The larvae were collected according to the methods described by Qian and Pechenik (1998). The tube of the adults was gently cracked with forceps to release the gametes. Oocytes were then mixed with the sperm and transferred to a new container with 500 mL FSW for fertilization. Larvae were reared on microalga *Isochrysis galbana* (Tahitian strain) after hatching. The seawater culture medium was replaced with fresh FSW and algae every day, and the trochophore-stage larvae reached the competent stage after 5 d of incubation at around 25° C.

Larvae Food and Cultivation

The diet for *A. amphitrite* and *H. elegans* cultivated in this study were *C. gracilis* and *Isochrysis galbana*, respectively. In the laboratory, the algae were cultured with Guillard's f/2 medium. The f/2 medium was prepared by adding designated amount of $NaNO_3$, $NaH_2PO_4H_2O$, trace metal solution and vitamin solution into autoclaved FSW (Guillard and Ryther, 1962), with an extra addition of $Na_2SiO_3$ $9H_2O$ for the cultivation of *C. gracilis*. Algal stocks were then added into the culture medium in a 2 L Erlenmeyer flask and subcultured bi-weekly. The cultures were bubbled and illuminated under 14 h/10 h light-dark cycle at 23° C. for incubation.

Settlement Bioassay of *A. amphitrite*

The test compounds were dissolved with a small amount of DMSO. The test compounds were used in six concentrations from 100 ppm to 3.125 ppm with 2-fold serial dilution. The same amount of DMSO was used as the negative control for all testing concentrations. Approximately 20±2 individual *A. amphitrite* cyprids were placed into each well of the 24-well polystyrene culture plate containing 2 mL of FSW and were subjected to different treatments. For all treatments and controls, three replicates were performed. The plates were then incubated at 25° C. in darkness. After 48 h, the number of settled and swimming larvae were counted using Leica MZ6 microscope, and possible toxic effects were also noted.

Settlement Bioassay of *H. elegans*

The test compounds were dissolved with a small amount of DMSO. The test compounds were used at six different concentrations with a 2-fold serial dilution from 100 ppm to 3.125 ppm. The same amount of DMSO was used as the negative control for all testing concentrations. Approximately 10±2 individuals of *H. elegans* larvae were put into each well of a 24-well polystyrene culture plate that contained 2 mL of FSW with different concentrations of test solution. Approximately $10^{-4}$ molarity of 3-isobutyl-1-methylxanthine was added into each well as an inducer to induce the settlement of *H. elegans* larvae (Xu et al., 2010). The plates were then incubated at 25° C. in darkness. After 24 h, the number of settled and swimming larvae were counted using Leica MZ6 microscope, and possible toxic effects were also noted.

Preparation of Polymer/Antifoulant Coatings

The polymer/antifoulant coatings in subject invention were prepared using the solution casting method described by Ding et al. 2018. The coating was prepared by dissolving poly(ε-caprolactone) based polyurethane (PCL-PU) and BOC-butenolide, in different proportions (i.e. 95 wt % polymer and 5 wt % antifoulant for 5% antifoulant coating), in xylene with vigorous stirring until all solids have dissolved to form a uniform solution. The solution was applied onto the surface of the panels, either epoxy panel (25 mm×75 mm) for release rate determination or PVC panels (53 mm×125 mm) for field test, and the panels were then placed under room temperature for all solvent to evaporate and form a continuous coating.

Determination of Antifoulant Release Rate from the Coatings

The release rate of BOC-butenolide was determined by HPLC for quantification. The polymer/antifoulant coatings were prepared on an epoxy panel (25 mm×75 mm). The coated panels were then put into ASW. At certain time points (day 1, 8, 15, 22, 29, 50, 71, 92 after immersion onto ASW), the panels were transferred to individual containers with 100 mL of fresh ASW. After immersing for 24 h, 10 mL of ASW with analyte in each of the containers was extracted with 10 mL of dichloromethane (DCM), the DCM fraction with the analyte was dried under nitrogen gas, and redissolved in 200 µL of methanol and subjected to HPLC analysis (Waters 2695, Taunton, Massachusetts, US) using a reversed-phase system with a C18 column (Phenomenex Luna C18(2), 250×4.6 mm, 5 microns, Torrance, California, US) and a photodiode array detector (Waters 2998, Taunton, Massachusetts, US) operated at 210 nm (ASTM D6903-07, 2013; Chen et al., 2015; Ma et al., 2017).

Field Test

The field tests were conducted at a fish farm in Yung Shue O, Hong Kong (114°21'E, 22°24'N) from January to March 2018. PVC panels (53 mm×125 mm) covered with coatings were immersed in seawater at a depth of 1 m from surface. The panels were retrieved once every month to be washed gently with seawater to remove dirt and photographed before being placed back in the sea. The antifouling potential of different panels was compared to determine the efficiency of the coatings. ImageJ (National Institutes of Health, Bethesda, Maryland, USA) was used to estimate the fouling coverage of the panels (Schneider et al. 2012). The percentage of area covered by foulers was calculated from the ratio of total fouling area to the panel area in which the area was highlighted by threshold function in ImageJ. All statistical analyses were carried out using IBM SPSS Statistics 22. One-way ANOVA was employed after initial analyses of heterogeneity and variance of dataset with Levene's test, followed by Tukey's post hoc test. Significance was defined as p value lower than 0.05.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Anti-Larval Settlement Performance

Figure 3:
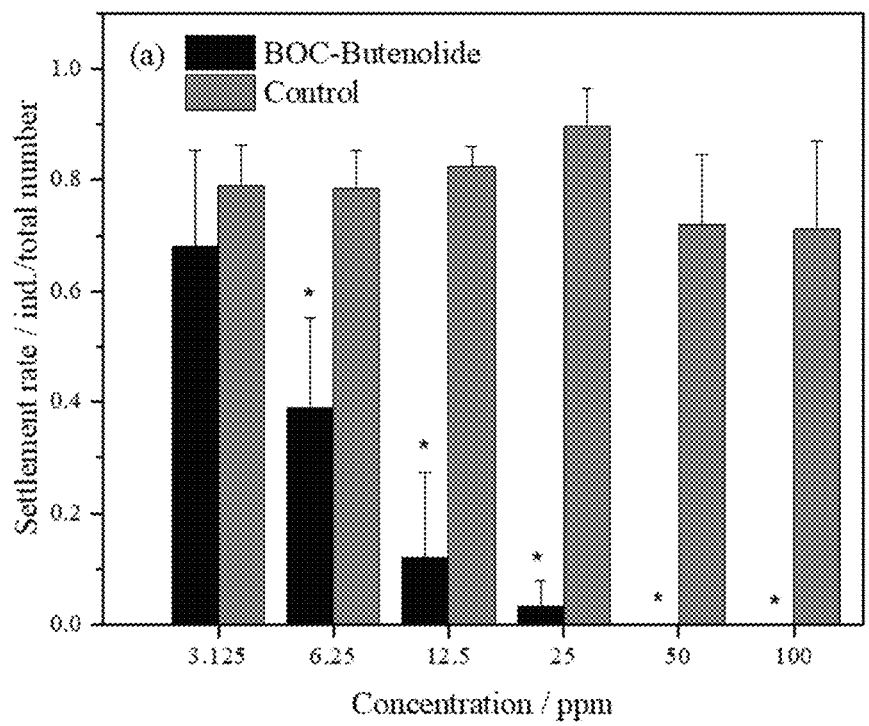
FIG. 3. *Balanus amphitrite* larval settlement rate of BOC-butenolide treatment. The asterisks indicate significant differences from the control with $p<0.05$.
Figure 4:
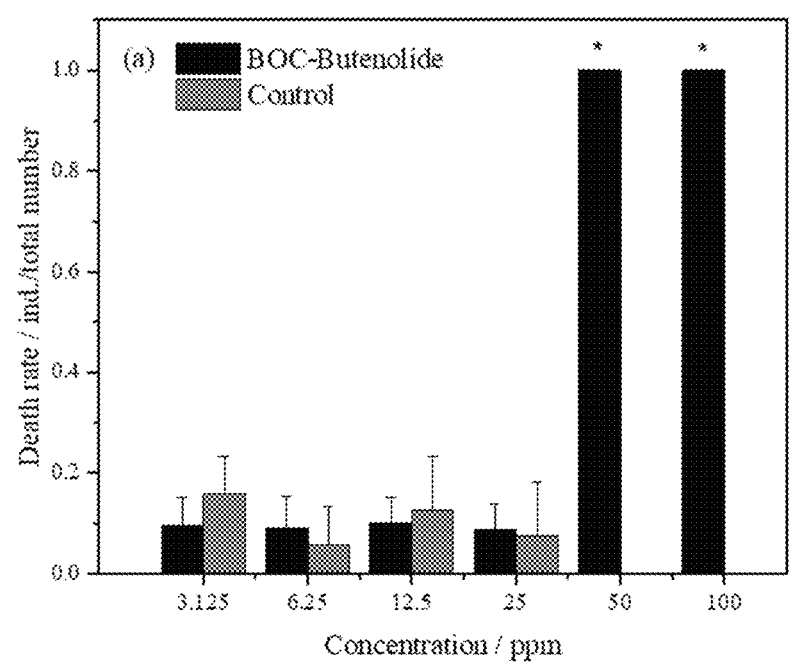
FIG. 4. *B. amphitrite* larval death rate of BOC-butenolide treatment. The asterisks indicate significant differences from the control with $p<0.05$.

To access BOC-butenolide (FIG. 1) antifouling (AF) activities, anti-larval settlement bioassays were conducted. Two marine invertebrate larvae, *Balanus amphitrite* and *Hydroides elegans*, were tested. At concentration of 50 to 100 ppm, BOC-butenolide inhibits the attachment of barnacle cyprids. The cyprids started to show some settlement at 25 ppm, at a rate of around 3%, and the settlement rate continuously increased, reaching around 70% settlement rate, at a concentration of 3.125 ppm (FIG. 3). It did not show any toxicity at 25 ppm and below (FIG. 4).

Figure 5:
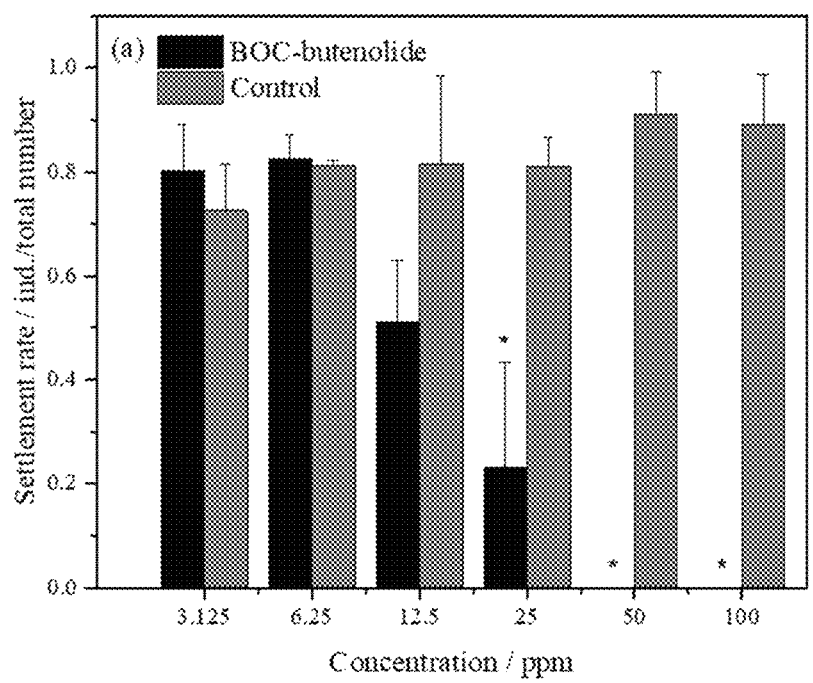
FIG. 5. *H. elegans* larval settlement rate of BOC-butenolide treatment. The asterisks indicate significant differences from the control with $p<0.05$.
Figure 6:
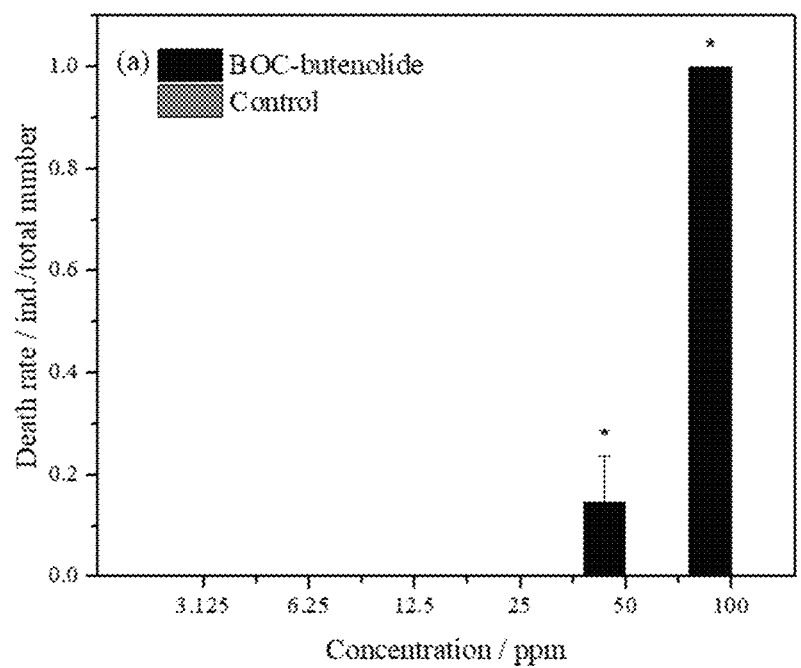
FIG. 6. *H. elegans* larval death rate of BOC-butenolide treatment. The asterisks indicate significant differences from the control with $p<0.05$.

For *H. elegans* larvae, there were no larval settlement at concentrations of 50 and 100 ppm, a significant difference with the control group was still observed at 25 ppm, with a settlement rate of around 20%. There is an increase in larval settlement from 25 ppm to 3.125 ppm, up to 80% settlement rate at 3.125 ppm (FIG. 5). It did not show any toxicity at 25 ppm and below, and it only showed around 10% of death at a concentration of 50 ppm (FIG. 6).

Example 2—Anti-Fouling Performance of Boc-Butenolide the Coating

Figure 7:
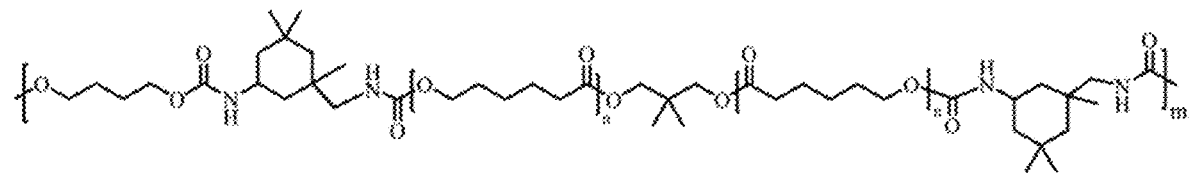
FIG. 7. Chemical structure of polymer matrix poly(ε-caprolactone) based polyurethane (PCL-PU).
Figure 8:
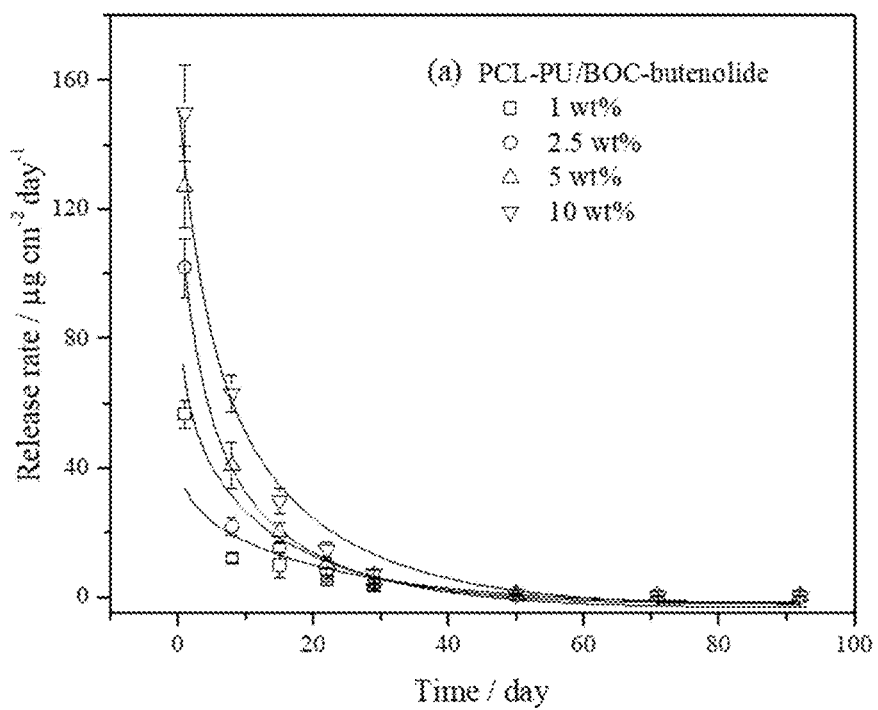
FIG. 8. Release rate measurement of BOC-butenolide with PCL-PU matrix for 90 days.
Figure 9:
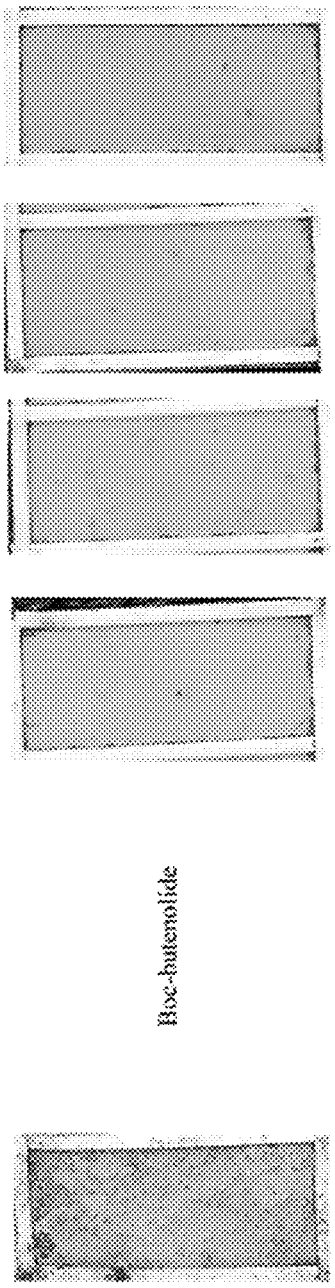
FIG. 9. Field test of various concentrations of BOC-butenolide and butenolide with PCL-PU matrix for 3 months. (From left to the right, Control, 1, 2.5, 5, 10 wt % of BOC-butenolide (top) or butenolide (bottom)). The test was continued for 2 months and retrieved at a monthly interval.
Figure 9:
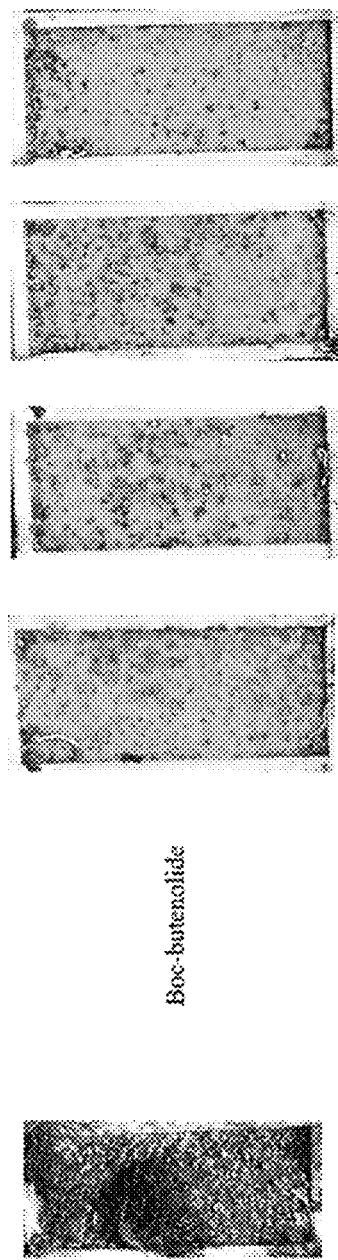

To evaluate the AF coating with BOC-butenolide as AF compound, we develop a coating using a biodegradable polymer, poly(ε-caprolactone) based polyurethane (PCL-PU) (FIG. 7). We tested the releasing ability of BOC-butenolide in the AF coating with artificial seawater (FIG. 8) together with the field test performance (FIG. 9). Generally, the amount of compounds released from the coatings at a particular time is positively correlated with the initial concentration of the compounds in the coatings, meaning that the release rate could be controlled by changing the concentration of antifoulant in the coatings. The initial release rate of BOC-butenolide was recorded to be 150 µg cm$^{-2}$ day$^{-1}$ and for 10 wt % samples, and the coating can still release BOC-butenolide for at least 2 months. For the field test, the results showed that BOC-butenolide has a relatively good AF ability to resist the attachment of the fouling organisms.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Almeida, J. R., & Vasconcelos, V. (2015). Natural antifouling compounds: Effectiveness in preventing invertebrate settlement and adhesion. Biotechnology Advances, 33, 343-357.

Alzieu C. 2000. Environmental impact of TBT: the French experience. Sci. Total Environ. 258:99-102.

ASTM D6903-07, Standard Test Method for Determination of Organic Biocide Release Rate from Antifouling Coatings in Substitute Ocean Water; ASTM International: West Conshohocken, PA, 2013.

Chen, L., Xu, Y., Wang, W., & Qian, P. Y. (2015) Degradation kinetics of a potent antifouling agent, butenolide, under various environmental conditions. Chemosphere, 119, 1075-1083.

Dahms, H. U., Xu Y., & Pfeiffer, C. (2006). Antifouling potential of cyanobacteria: a mini-review. Biofouling, 22, 317-327.

Ding, W., Ma, C., Zhang, W., Chiang, H., Tam C., Xu, Y., Zhang, G., Qian, P. Y. (2018). Anti-biofilm effect of a butenolide/polymer coating and metatranscriptomic analyses. Biofouling, 34, 111-122.

Dobretsov, S., Dahms, H. U., & Qian, P. Y. (2006). Inhibition of biofouling by marine microorganisms and their metabolites. Biofouling, 22(1), 43-54.

Fusetani, N. (2011). Antifouling marine natural products. Natural Product Reports, 28,400.

Greene, N. (2007). Computational Models to Predict Toxicity. Comprehensive Medicinal Chemistry II, 909-932.

Guha R. (2013). On exploring structure-activity relationships. Methods in Molecular Biology, 993, 81-94.

Guillard, R. R. L., & Ryther, J. H. (1962). Studies of marine planktonic diatoms. I. Cyclotella nana Hustedt and Detonula confervacea Cleve. Canadian Journal of Microbiology, 8, 229-239.

Harder, T. N., Thiyagarajan, V., & Qian, P. Y. (2001). Effect of cyprid age on the settlement of Balanus amphitrite darwin in response to natural biofilms. Biofouling, 17, 211-219.

Konstantinou I K, Albanis T A. 2004. Worldwide occurrence and effects of antifouling paint booster biocides in the aquatic environment: a review. Environ. Int. 30:235-248.

Li, Y., Zhang, F., Xu, Y., Matsumura, K., Han, Z., Liu, L., Lin, W., Jia, Y., & Qian, P. Y. (2012). Structural optimization and evaluation of butenolides as potent antifouling agents: modification of the side chain affects the biological activities of compounds. Biofouling, 28, 857-864.

Ma, C., Zhang, W., Zhang, G., & Qian, P. Y. (2017) Environmentally friendly antifouling coatings based on biodegradable polymer and natural antifoulant. ACS Sustainable Chemistry & Engineering, 5, 6304-6309.

Qian, P. Y., & Pechenik, J. A. (1998). Effects of larval starvation and delayed metamorphosis on juvenile survival and growth of the tube-dwelling polychaete Hydroides elegans (Haswell). Journal of Experimental Marine Biology and Ecology, 27, 169-185.

Qian, P. Y., Lau, S. C., Dahms, H. U., Dobretsov, S., & Harder, T. (2007). Marine biofilms as mediators of colonization by marine macroorganisms: implications for antifouling and aquaculture. Marine Biotechnology, 9(4), 399-410.

Qian, P. Y., Xu, Y., & Fusetani, N. (2010). Natural products as antifouling compounds: recent progress and future perspectives. Biofouling, 2010-223-234.

Qian, P. Y., Li, Z., Xu, Y., Li, Y., & Fusetani, N. (2015). Mini-review: Marine natural products and their synthetic analogs as antifouling compounds: 2009-2014. Biofouling, 31(1), 101-122

Schneider, C. A., Rasband, W. S., & Eliceiri, K. W. (2012). NIH Image to ImageJ: 25 years of image analysis. Nature Methods, 9(7), 671-675.

Xu, Y., He, H., Schulz, S., Liu, X., Fusetani, N., Xiong, H., Xiao, X., & Qian, P. Y. (2010). Potent antifouling compounds produced by marine Streptomyces. Bioresource Technology, 101, 1331-1336.

Yebra D M, Kiil S, Dam-Johansen K. 2004. Antifouling technology—past, present and future steps towards efficient and environmentally friendly antifouling coatings. Prog Org Coat. 50:75-104.

We claim:

1. A method for enhancing the performance and/or longevity of an object or surface, said method comprising contacting or applying an effective amount of a composition comprising BOC-butenolide according to formula (I) to a surface and/or an object:

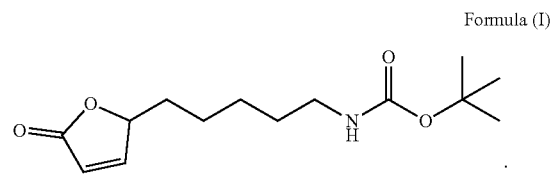 [SMILES: CC(C)(C)OC(=O)NCCCCCC1C=CC(=O)O1]

Formula (I)

2. The method of claim 1, further comprising releasing the BOC-butenolide from the composition after application to the object and/or surface at a rate of about 140 µg cm$^{-2}$ day$^{-1}$ to about 150 µg cm$^{-2}$ day$^{-1}$.

3. The method of claim 1, wherein the performance and/or longevity is enhanced by one or a combination of the following:
   a) inhibiting, limiting, or ceasing corrosion;
   b) inhibiting fouling by living organisms or non-living substances;
   c) inhibiting abrasion; or
   d) cleaning.

4. The method of claim 1, wherein the composition further comprises a coating component.

5. The method of claim 4, wherein the coating component is a polymer, binder, pigment, solvent, buffering agent, or any combination thereof.

6. The method of claim 5, wherein the polymer is a Poly(ε-caprolactone)-based polymer, according to formula (II):

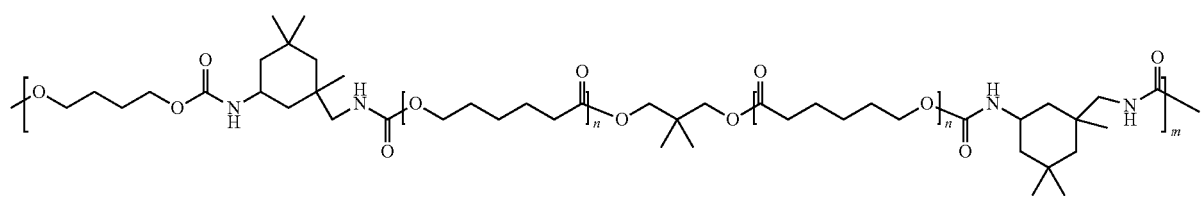

Formula (II)

wherein n is about 1 to about 10 and m is about 1 to about 10.

7. The method of claim 1, wherein the surface and/or object is submerged in water or is a medical device.

8. The method of claim 7, wherein the submerged surface and/or object is a ship, hull, tubing, pipe, pump, propeller, buoy, or rope.

9. A composition, comprising BOC butanolide according to Formula (I):

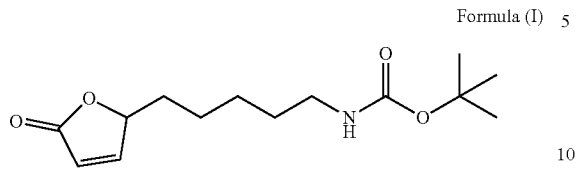

Formula (I)

and at least one coating component wherein the coating component is a Poly(ε-caprolactone)-based polymer, according to formula (II):

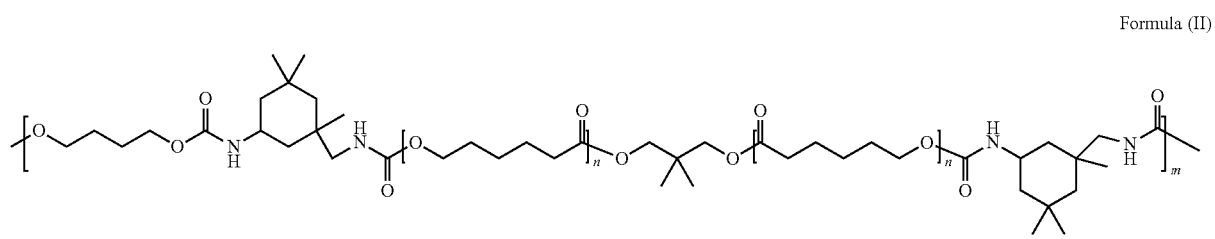

Formula (II)

wherein n is about 1 to about 10 and m is about 1 to about 10.

10. The composition of claim 9, wherein the composition is a paint, stain, adhesive, primer, sealant, finish, varnish, polish, lacquer, anti-fouling substance, and/or anti-abrasive substance.

11. The composition of claim 10, wherein the BOC-butenolide is at a concentration of about 25 μg/mL and the polymer is at a concentration of about 80% to about 99%.

* * * * *